US008900166B2

(12) United States Patent
Spector (10) Patent No.: US 8,900,166 B2
(45) Date of Patent: Dec. 2, 2014

(54) AUTOMATIC ADJUSTABLE VOLTAGE TO STABILIZE PRESSURE FOR SHOCKWAVE MEDICAL THERAPY DEVICE

(76) Inventor: Avner Spector, Savyon (IL)

(*) Notice: Subject to any disclaimer, the term of this patent is extended or adjusted under 35 U.S.C. 154(b) by 468 days.

(21) Appl. No.: 12/937,546

(22) PCT Filed: Apr. 5, 2009

(86) PCT No.: PCT/IL2009/000375
§ 371 (c)(1),
(2), (4) Date: Oct. 13, 2010

(87) PCT Pub. No.: WO2009/128061
PCT Pub. Date: Oct. 22, 2009

(65) Prior Publication Data
US 2011/0028868 A1 Feb. 3, 2011

Related U.S. Application Data

(60) Provisional application No. 61/071,113, filed on Apr. 14, 2008.

(51) Int. Cl.
*A61B 17/225* (2006.01)
*G10K 15/06* (2006.01)

(52) U.S. Cl.
CPC ............ *G10K 15/06* (2013.01); *A61B 17/2255* (2013.01); *A61B 17/225* (2013.01)
USPC .................................... 601/2; 601/4; 367/147

(58) Field of Classification Search
USPC .............................. 601/2–4; 600/439; 367/147
See application file for complete search history.

(56) References Cited

U.S. PATENT DOCUMENTS

| 3,442,531 | A | | 5/1969 | Rutledge |
| 3,942,531 | A | | 3/1976 | Hoff et al. |
| 4,722,340 | A | | 2/1988 | Takayama et al. |
| 4,730,614 | A | | 3/1988 | Lacruche et al. |
| 4,763,652 | A | * | 8/1988 | Brisson et al. ............ 601/4 |
| 5,109,338 | A | | 4/1992 | Ermert et al. |

(Continued)

FOREIGN PATENT DOCUMENTS

| DE | 1031159 | 9/2004 |
| EP | 0359863 | 3/1990 |
| EP | 0911804 | 4/1999 |

OTHER PUBLICATIONS

Angehm Fiorenzo et al, Can cellulite be treated with low-energy extracorporeal shock wave therapy, Clinical Interventions in Aging 2007:2(4) 623-630.

(Continued)

*Primary Examiner* — Ruth S Smith
(74) *Attorney, Agent, or Firm* — Graeser Associates International Inc; Dvorah Graeser (57) ABSTRACT

An electrohydraulic shock-wave therapy apparatus comprising a variable voltage source and a controller that controls the voltage source for accurate adjustment of the shock wave pressure. The invention, in various embodiments, also includes various methods, optionally closed loop as well as open loop based, for determining the shock pressure while compensating for burnout and or erosion that normally suppress the pressure after some thousands of sparks. This way the effective lifetime of the electrodes is dramatically extended. The control is further used for significantly increasing the effective therapeutic area of the apparatus by adjusting the shock pressure value close to the maximal safe value.

13 Claims, 7 Drawing Sheets

(56) References Cited

U.S. PATENT DOCUMENTS

| | | |
|---|---|---|
| 6,217,531 B1 | 4/2001 | Reitmajer |
| 2005/0113722 A1 | 5/2005 | Schultheiss |
| 2006/0036168 A1 | 2/2006 | Liang et al. |

OTHER PUBLICATIONS

International Search Report for PCT/IL2009/000375, mailed Oct. 15, 2009.
Office Action for Chinese Application 200980121406.2, mailed Apr. 28, 2012.

* cited by examiner

Typical pulse shape and time domain representation
at peak pressure for shockwave

Figure 4

Schematic presentation of
the Pressure attenuation vs. Number of SW

AUTOMATIC ADJUSTABLE VOLTAGE TO STABILIZE PRESSURE FOR SHOCKWAVE MEDICAL THERAPY DEVICE

CROSS-REFERENCE TO RELATED APPLICATIONS

This application is the U.S. national phase application of PCT International Application No. PCT/IL2009/000375, filed on Apr. 5, 2009, which claims the benefit of U.S. Provisional Application Ser. No. 61/071,113, filed on Apr. 14, 2008, all of which are hereby incorporated by reference in their entirety as if fully set forth herein.

FIELD OF THE PRESENT INVENTION

The present invention relates to systems and methods that use an acoustic shock-wave technique for medical therapy. In particular, it relates to enhanced efficiency spark gap based extracorporeal shock-wave therapy technology.

BACKGROUND OF THE PRESENT INVENTION

Pressure-pulse therapy, also known as shock-wave (SW) therapy, is a non invasive extracorporeal technique that is used in many medical applications e.g.: Pulverizing kidney stones and calculi in the bladder and urethra (lithotripsy); Myocardial revascularization in cardiovascular treatments; Cerebral embolism treatment; Orthopedic and sports medicine applications such as rehabilitation of joints, bones, calcifying tendonitis of the rotator cuff, humeral epicondylitis, plantar fasciitis and musculoskeletal problems; Wound healing; Dissolving lipids in cells close to the skin and in the pelvic region, as described in U.S. Pat. No. 3,942,531; Remodeling of the collagen within the dermis using defocused low-energy extracorporeal shock waves (ESW), as was shown by ANGEHRN F. et al, Can cellulite be treated with low-energy extracorporeal shock wave therapy? Clinical Interventions in Aging 2007: vol. 2(4) pp. 623-630; and more.

The shock-wave is generated by an electric storage capacitor that is charged with a very high voltage and subsequently rapidly discharged via an electroacoustic transducer. This electrohydraulic or spark-gap transducer based technique for acoustic shock-wave generation, which is the basis of the present invention, provides for a relatively low cost and compact apparatus. However, the life span of such devices is typically limited to a few thousands of shock-waves due to electrode erosion over a period of use.

Various solutions have been proposed in an attempt to overcome this problem. U.S. Pat. No. 4,730,614 describes a basic solution to the problem of erosion, involving manually adjusting the electrode position. U.S. Pat. No. 6,217,531 describes a solution in which two electrodes are used in the pressure pulse therapy device. As the electrodes become eroded due to use, the distance between the electrodes is mechanically, physically adjusted in order to maintain the original spark gap, or distance between the electrodes. The adjustments are performed automatically. Clearly, manually adjusting the distance between the electrodes is not practical. However, even an automatic control of the mechanical adjustment is not useful because it involves expensive, delicate and complicated equipment. Moreover, mechanical movement of the electrodes can cause other problems, such as improper deviation of the electrode position.

Alternative shock-wave generation method is based on piezoelectric transducer, making use of the fact that polycrystalline piezoelectric ceramic elements expand or, depending on the high-voltage polarization, contract when subjected to a high-voltage pulse. Due to the spherical arrangement of a great number of piezoelectric crystals, the waves thus generated are focused on the center, i.e. the focus, of the spherical arrangement. The advantage of long service life is achieved at the expense of cumbersome and expensive equipment. In addition to this, X-ray localization systems are rather difficult to integrate into piezoelectric systems.

An alternative method is the electromagnetic based system in which a strong pulsed current flows through a flat coil, thus generating a rapidly changing magnetic field. An opposing magnetic field is induced in a metal membrane located above the coil, thus pushing the membrane away from the coil. The initially flat waves are focused by means of a lens array that is arranged above the coil. Also in this method, the longer service life is achieved at the expense of equipment complexity and cost.

An additional drawback of the existing electrohydraulic devices is that in vascular and soft tissue applications, where the chock intensity is relatively limited, the achieved effective therapeutic surface area of the generated shock-wave at the distant focal point within the human body is correspondingly low.

SUMMARY OF THE PRESENT INVENTION

The background art does not teach or suggest how to maintain a stable pressure shock-wave throughout long lifetime of an electrohydraulic shock generator, nor does it suggest how to increase its effective therapeutic surface area at low shock intensity levels.

The present invention overcomes these deficiencies of the background art by providing an automatically adjustable charging voltage electrohydraulic therapy apparatus. The adjustable voltage stabilizes the shock-wave pressure and or energy density by compensating for the electrode burnout and or erosion with higher charging voltage without requiring physical movement of the electrode position. Furthermore, the subtle charging voltage adjustment would prevent any pressure fluctuations that may occur over operation time. In a specific embodiment, the pressure may be further adjusted to an optimal level in which the resulting effective therapeutic surface area of the shock wave is maximized.

The present invention resolves the above described drawbacks of the electrohydraulic method while preserving its inherent advantages, i.e. simplicity, compactness and low cost.

A shock-wave pulse is characterized by an initial sharp rise in pressure, followed by a high pressure level, which is not necessarily constant, and then a fast reduction in pressure. Each pulse therefore has a life time, maximal pressure level, average pressure level, and total energy, all of which are preferably maintained at a desired level, more preferably at a constant desired level according to the present invention.

The charging voltage can be continuously adjusted at real time during the operation of the invented apparatus according to any one of the following methods representing various embodiments of the present invention or to any combination thereof or to any weighted average of any combination of the criteria associated thereof:

1. "Measured shock pressure controlled closed loop": The resulting shock pressure is measured a plurality of times, and is preferably constantly measured during normal operation of the apparatus by a pressure transducer. The charging voltage is correspondingly adjusted at real time to always retain the pressure at a desired level.

2. "Shock number calibration graph": For a given apparatus model, which is intended for a specific therapeutic application, a sample quantity of units is tested at the factory. The required shock pressure is measured by a pressure transducer. Each unit is operated for a large number of shocks that spans the full lifetime of the apparatus. The charging voltage is increased to compensate for the shock-wave pressure suppression that results due to electrode erosion, thus retaining the required pressure value at the pressure transducer. The resulting required charging voltage as a function of the shocks number defines the required "Shock number calibration graph". During normal operation of the apparatus the charging voltage is adjusted a plurality of times, and is preferably constantly adjusted according to the wave-shock number and the predefined calibration graph. It should be noted that as used herein, the term "graph" optionally refers to any calibration mapping, including but not limited to a graph, a table, a list, a mathematical function and so forth.

3. "Inter electrode gap calibration graph": A sample quantity of units is tested in the same conditions as in 2 above. In addition, the inter-electrode gap is measured a plurality of times, and is preferably continuously measured by some optical measuring device. The resulting graph of the required charging voltage, as a function of the measured gap, defines the required "inter-electrode gap calibration graph". The gap is measured a plurality of times, and is preferably constantly measured, also during normal operation of the apparatus and the charging voltage is adjusted according to it and the predefined calibration graph.

4. "Drop time delay calibration graph": A sample quantity of units is tested in the same conditions as in 2 above. In addition, the delay time between the spark trigger instant to the falling edge of the spark electrodes input voltage waveform, i.e. spark start time, is monitored and preferably is continuously monitored. The resulting graph of the required charging voltage, as a function of the monitored delay time defines the required "drop time delay calibration graph". The delay is monitored, optionally a plurality of times but preferably constantly, also during normal operation of the apparatus and the charging voltage is adjusted according to it and to the predefined calibration graph. Note that in a specific case the calibration graph based mechanism may optionally be substituted by a close control loop that would retain the delay fixed by charging voltage variations to compensate for the electrode erosion over time.

5. "Voltage tilt calibration graph": A sample quantity of units is tested in the same conditions as in 2 above. In addition, the spark electrodes input voltage tilt amount between its raising and falling edges is monitored, preferably constantly monitored. The resulting graph of the required charging voltage, as a function of the monitored tilt, defines the required "voltage tilt calibration graph". The tilt is measured a plurality of times, and is preferably constantly measured also during normal operation of the apparatus, and the charging voltage is adjusted according to it and to the predefined calibration graph. Note that in a specific case the calibration graph based mechanism may be substituted by a close control loop that would retain the tilt fixed by charging voltage variations to compensate for the electrode erosion over time.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or stages manually, automatically, or a combination thereof. Moreover, according to actual instrumentation and equipment of preferred embodiments of the method and system of the present invention, several selected stages could be implemented by hardware or by software or by any operating system of any firmware or a combination thereof. For example, as hardware, selected stages of the invention could be implemented as a chip or a circuit. As software, selected stages of the invention could be implemented as a plurality of software instructions being executed by a computer using any suitable operating system. In any case, selected stages of the method and system of the invention could be described as being performed by a data processor, such as any computing platform for executing a plurality of instructions.

BRIEF DESCRIPTION OF THE DRAWINGS

The present invention will be more clearly understood from the accompanying detailed description and drawings, in which same number designations are maintained throughout the figures for each element. The invention is herein described, by way of an example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

DETAILED DESCRIPTION OF PREFERRED EMBODIMENTS

The present invention, in at least some embodiments, is of an adjustable voltage apparatus for a pulse pressure therapy apparatus which compensates for electrode erosion without requiring physical movement of the electrode position. The present invention instead provides for an adjustment to the input energy to the electrode apparatus according to the degree of erosion, thereby providing a steady required output pressure for pressure pulse therapy. Optionally, the adjustment is made according to a predetermined level over time; alternatively and preferably, the adjustment is made according to one or more measurements of the inter electrode gap and or of one or more functions of the apparatus, more preferably according to one or more measurements of the output pressure. Preferably the voltage is automatically adjusted in order to achieve constant pressure and a longer working time period for the electrodes in such a device.

The principles and operation of a device, a system and a method according to the present invention may be better understood with reference to the drawings and the accompanying description, it being understood that these drawings are given for illustrative purposes only and are not meant to be limiting.

Figure 1:
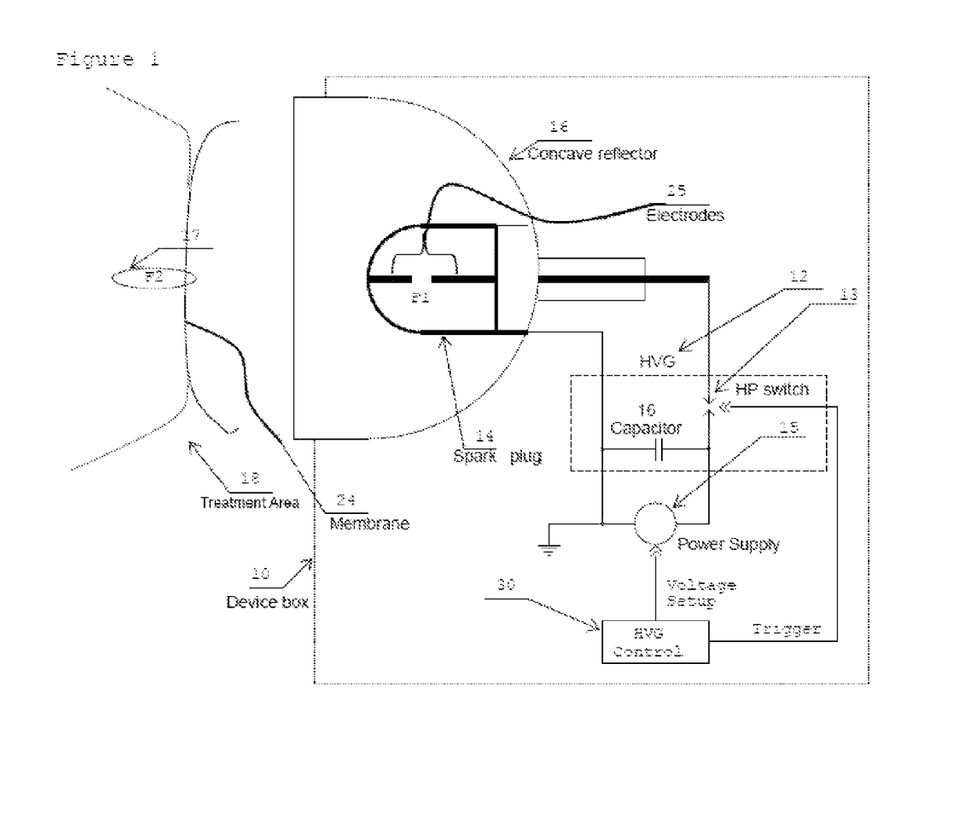
FIG. 1 is a schematic representation of an exemplary shock wave therapy device according to the present invention.

Referring now to the drawings, FIG. 1 is a schematic block diagram of an illustrative, exemplary device according to the present invention for generating therapeutic acoustic shock waves. As shown, a device box 10 comprises a high voltage Power Supply 15 that charges a high voltage capacitor 16. Pulse generator HVG 12 is structured as is known in the art (for example with regard to U.S. Pat. No. 3,442,531, hereby incorporated by reference as if fully set forth herein). Pulse generator 12 preferably contains a high voltage/high power gated switch 13, which may be implemented without limitation by a spark gap switch. Pulse generator 12 generates an electrical pulse by closing HP switch 13 and thus discharging the capacitor 16 into spark plug 14. Spark plug 14 comprises two common axis electrodes with a narrow gap between their tips, which are immersed in a liquid, of which the electrical pulse creates plasma, which in turn causes an acoustic shock-wave to be produced. The shock-wave expands radially from spark plug 14 until it strikes a concave reflector 16, which is optionally and preferably an ellipsoid. Alternatively, concave reflector 16 may have any geometric shape with similar F2 17 focal properties.

Concave reflector 16 focuses the shock-wave generated at a focal point F1, and reflects it to focal point (Zone) F2 17 (the second focus of the ellipse) at a portion of the body of the patient, shown as a treatment area 18. Treatment area 18, for example, may optionally be a vascular structure, kidney (for example for pulverizing of kidney stones), shoulder or any other joint, or any other part of the body.

Commonly, in order to prevent leakage of fluids, a flexible membrane 24 is preferably used to shield spark plug 14 and concave reflector 16. The volume between spark plug 14 and concave reflector 16 is then preferably filled with a liquid such as water or other material, in order to provide an efficient acoustic coupling to the patient body. An acoustic coupling material (not shown in the drawing) is preferably located between flexible membrane 24 and the treatment area 18 against which flexible membrane 24 is pressed. The acoustic coupling mechanism may optionally be a gel.

The size of spark plug 14 gap is related to the distance between electrode 25 tips. As electrodes 25 erode over time throughout use, the size increases. However, this leads to a reduction of efficiency of shock-waves generation. Therefore, high voltage pulse generator 12 preferably features a power adjustment HVG control module 30 for adjusting the input voltage in order to compensate for the eroded electrodes. Power control module 30 may optionally adjust the voltage according to one or more of the following methods or to any combination of such methods or to any weighted average of any combination of the following methods according to various embodiments of the present invention as described above: 1. Measured shock pressure controlled closed loop, 2. Shocks number calibration graph, 3. Inter electrode gap calibration graph, 4. Drop time delay calibration graph and 5. Voltage tilt calibration graph.

Figure 2:
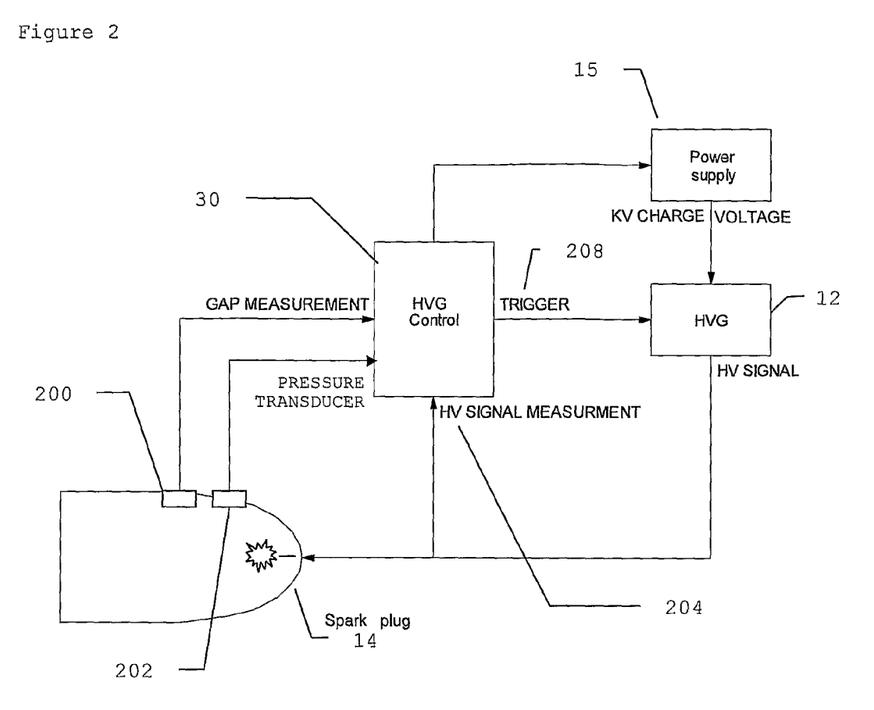
FIG. 2 illustrates the device of FIG. 1 where stabilization control, related signals and members are further detailed.

FIG. 2 depicts the device of FIG. 1 where stabilization control related signals and members are further detailed. As shown, the electrode apparatus preferably features a gap measurement apparatus 200 and a pressure transducer 202, for providing information regarding the status of the electrodes (not shown). Optionally, only one or none of these two components is present. For example, if pressure transducer 202 is used, then pressure transducer 202 determines the intensity of the pressure pulses that are generated through the application of HV signal voltage 204 to spark plug 14. Controller 30 may optionally compare the output pressure to the desired level and dictate accordingly to Power Supply 15 if and how the charging voltage to HVG 12 should be adjusted. Normally it will be gradually increased throughout the apparatus lifetime in order to compensate for the electrode erosion. An increased charging voltage would generate an increased HV signal 204 at HVG 12 output, thus a stronger spark and shock-wave would result at spark plug 14. HVG control 30 also triggers the sparks by a trigger signal 208 that HVG control 30 transfers to HVG 12. Both the desired pressure level and trigger rate can be programmed at HVG control 30.

Similarly, gap measurement apparatus 200 may optionally also be used to measure another aspect of the functioning of the electrodes, for example by featuring an optical measuring device to measure the width of the gap between the electrode tips. As the gap increases, such information is provided to controller 30, which again increases the amount of Power Supply 15 output voltage as previously described. Controller 30 may optionally include a microprocessor or a microcomputer, or any equivalent device or combination of components.

Figure 3:
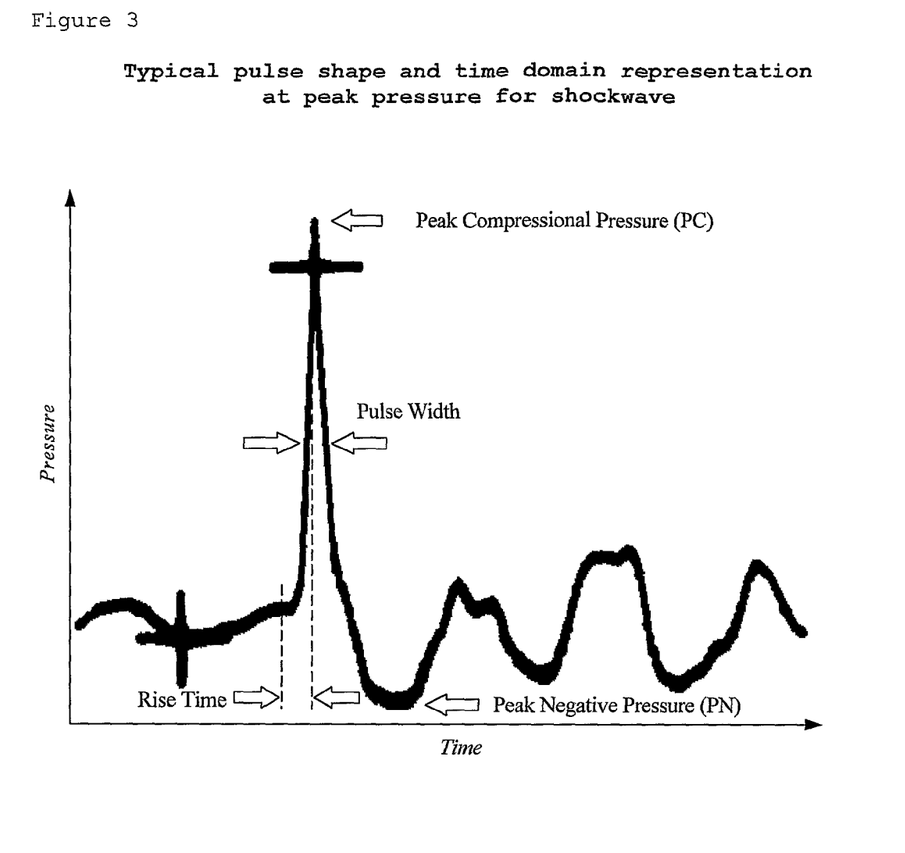
FIG. 3 illustrates a schematic graphical representation of a shock wave pressure pulse used in the present invention.

FIG. 3 illustrates a schematic graphical representation of a pressure pulse for use with the present invention. Typical pulse parameters are depicted like rise time, peak pressure, pulse width, and peak negative pressure.

Figure 4:
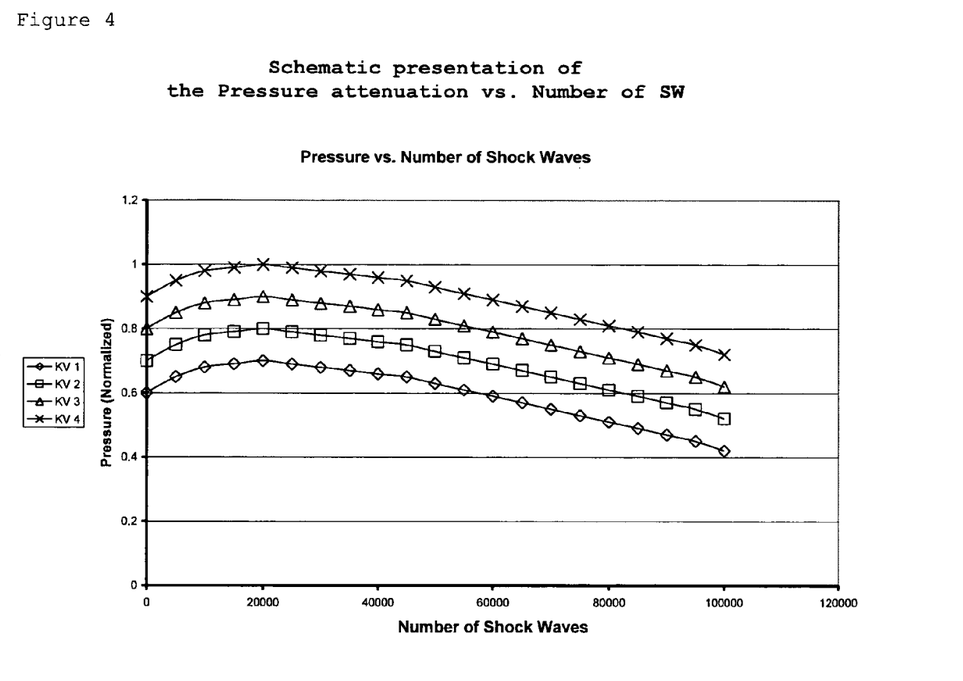
FIG. 4 illustrates a graphical presentation of shock-wave pressure changes vs. the number of generated shock-waves over the lifetime of a pair of electrodes with the charging voltage as a parameter.

FIG. 4 illustrates a graphical representation of shock-wave pressure variations vs. the number of generated shock-waves with regard to the charging voltage over the lifetime of a pair of electrodes. Pressure values are normalized to the maximal pressure value. Higher voltage value yields a higher pressure curve throughout the electrodes lifetime. It is also shown that for a constant voltage, the pressure increases during the first 20,000 sparks but then constantly decreases as a function of the number of sparks. To maintain a constant pressure, therefore, the voltage is preferably adjusted over the lifetime of the electrodes. It should be noted that electrode burnout as shown on the graphs of FIG. 4 is determined for a specific type of electrode and that different electrodes, with different shape and/or dimensions and/or materials, could give different effects. These graphs were generated during the life time of the electrodes at different constant voltages; however, they can optionally be used for automatic adjustment of the variable charging voltage through a software based algorithm. Such algorithm can optionally be implemented in control module 30 as previously described.

As a numerical example, assume that a constant normalized pressure level of 0.8 is required throughout the apparatus lifetime. At the beginning of the lifetime of the electrodes, at KV-3, the pressure level is 0.8. Later, after 20,000 shocks, the correct graphical level is shown at KV-2 level in order to retain the same pressure value. Similarly, after an additional 35000 shocks (55,0000 in total) switching back to KV-3 level is required, and after an additional 25000 shocks, switching to KV-4 level is required.

Figure 5:
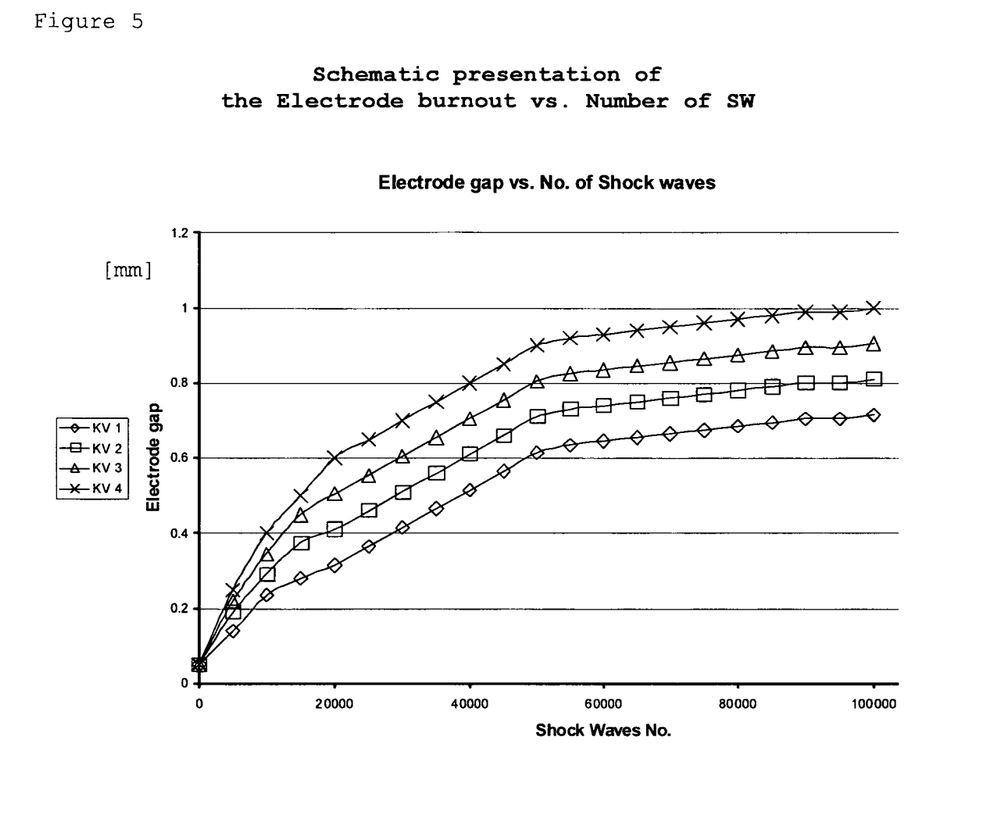
FIG. 5 illustrates a graphical representation of electrode burnout vs. the number of generated shock-waves over the lifetime of a pair of electrodes with the charging voltage as a parameter.

FIG. 5 illustrates a graphical representation of electrode burnout over lifetime vs. the number of generated shockwaves with the charging voltage as a parameter. The burnout is expressed by the inter-electrode gap width in mm.

FIG. 5 may also optionally be used as follows to determine future expected input voltages: When building a mathematical model of the graphs in FIG. 5, the number of shocks (N) is to be used as a parameter. N could be calculated, numerically or graphically, according to the erosion rate, plus the incremental addition of any additional sessions. Assuming that the source has already caused 20000 shocks at KV-4 level, the expected gap is 0.6 mm. Current treatment is to be performed at KV-2 level for 20000 shocks. To calculate the erosion at the end of the current session, FIG. 5 is used; on KV-2 level graph, the number of shocks that result in a gap of 0.6 mm is 40000 shocks. The value of 20000 shocks of the current session is then added to this number, resulting in 60000 shocks in total, resulting in gap of about 0.75 mm. Hence, the additional erosion at KV-2 level for 20000 shocks is 0.15 mm.

Furthermore, when planning the next treatment session, by knowing the current gap size, the number of shocks to be provided, and the pressure, FIG. 5 (or a similar type of graph) could be used to locate the most suitable KV level for this session.

Figure 6:
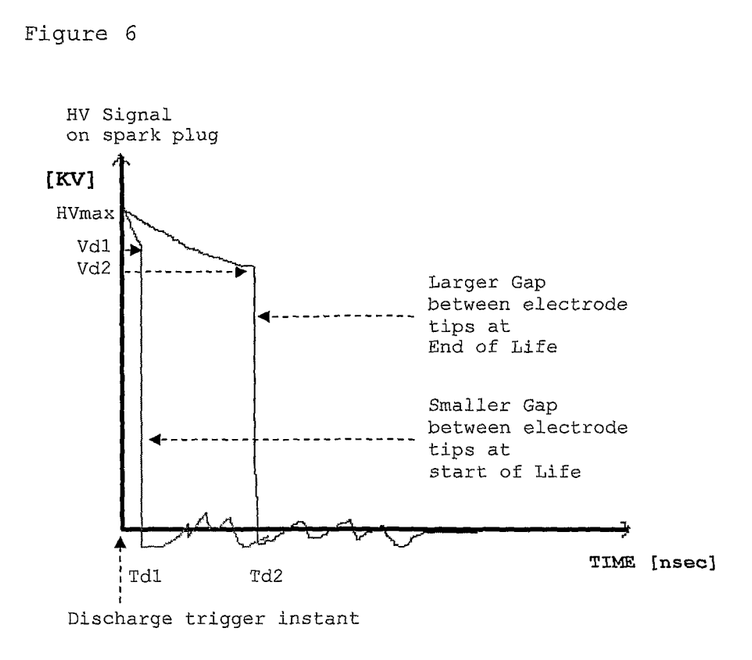
FIG. 6 illustrates typical electric voltage waveforms on the spark plug (HV Signal) at electrodes start of life and end of life.

FIG. 6 depicts a typical electric voltage waveform 204 on the spark plug (HV Signal) at electrodes start of life and end of life. At start of life the HV slightly descends after the trigger from HVmax to Vd1 during a short delay Td1 and then abruptly drops to zero as the spark occurs. At end of electrodes life the tilt from HVmax down to Vd2 is larger as well as the delay until the spark instant. The amount of either the tilt and or the delay may optionally be monitored on a typical apparatus in conditions of constant desired shock pressure and be later used as calibration graphs for control unit 30.

Figure 7:
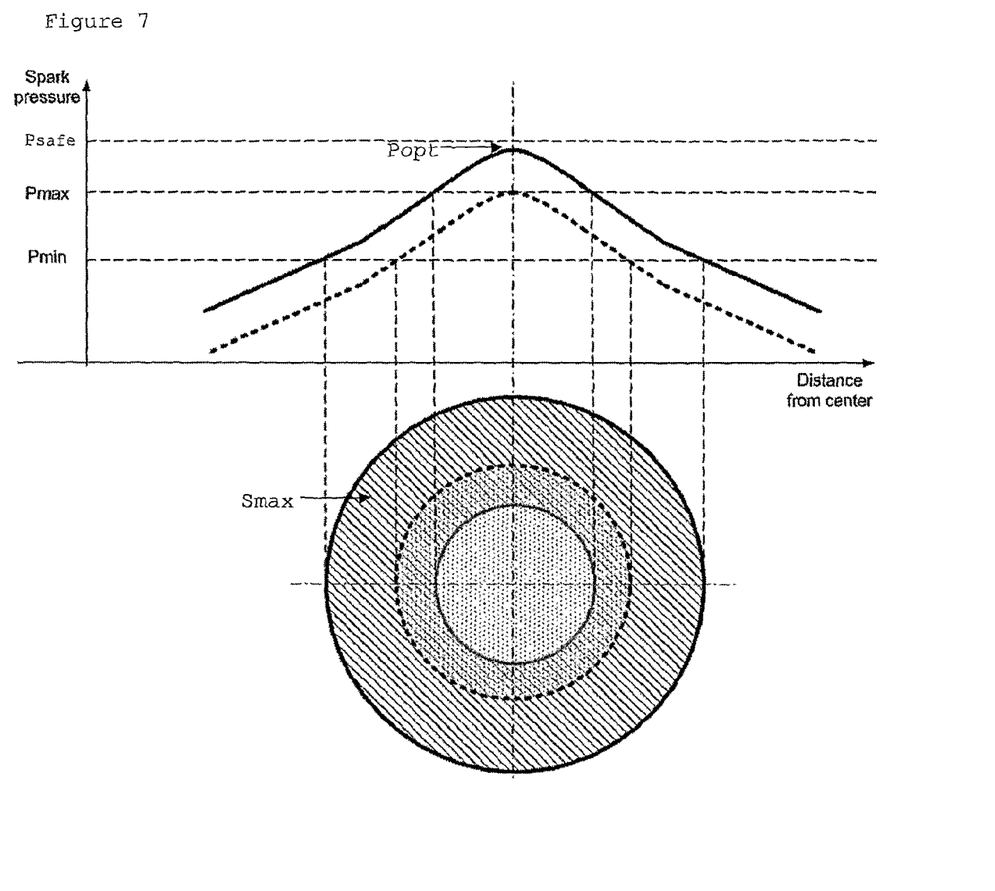
FIG. 7 illustrates how a maximal therapeutic area may be affected by fine tuning of the shock pressure value.

FIG. 7 illustrates how the therapeutic area may be maximized in the present invention by fine tuning of the shock peak pressure to an optimal value using variable charging voltage. The optimal pressure, denoted as Popt in the drawing, is higher than the maximal therapeutic pressure Pmax but lower than the maximal safe pressure Psafe. The achieved maximal therapeutic area Smax is depicted in FIG. 7 by the lined circular surface and is larger than the dotted area that is obtained when the peak pressure is Pmax. Popt is retained in normal operation by at least one of the above mentioned methods for desired pressure retention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An electrohydraulic shock-wave therapy apparatus providing constant pressure extracorporeal shock-waves, the apparatus comprising:
a high voltage power supply that is functionally coupled to and charges a high voltage capacitor;
wherein said capacitor is functionally connected to a spark plug wherein said connection is mediated with a pulse generator;
said spark plug having two common axis electrodes separated by a narrow gap between tips of the electrodes, said tips of said electrodes provided to generate said constant pressure extracorporeal shock-waves to form generated constant pressure extracorporeal shock-waves when said capacitor is discharged;
said pulse generator having a high voltage gated spark gap switch utilized to cause said capacitor to discharge into said spark plug; wherein said pulse generator is controlled with a controller module for adjusting an input voltage provided to said spark plug; wherein said controller module monitors a number of said generated constant pressure extracorporeal shock-waves;
wherein said spark plug is positioned adjacent to a concave reflector surface such that said generated constant pressure extracorporeal shock-waves expand radially from said spark plug and strike said concave reflector surface utilized to focus and transfer said generated constant pressure extracorporeal shock-waves toward a focal point;
wherein the apparatus is characterized in that said controller module automatically controls and adjusts the input voltage provided to said spark plug, in order to compensate for electrode erosion of said tips without movement of said tips; and wherein said input voltage is controlled according to the number of generated constant pressure extracorporeal shock waves using a predefined shock number calibration graph, wherein automatic control and adjustment-of the input voltage occurs substantially in real time.

2. The apparatus of claim 1 further comprising a gauge for measuring an inter electrode gap width and transferring a measured inter electrode gap width value to said controller module, wherein said controller module further adjusts the input voltage according to the measured inter electrode gap width value using a predefined inter electrode gap calibration graph.

3. The apparatus of claim 2, wherein said gauge comprises an optical measuring device.

4. The apparatus of claim 1 wherein said controller module further monitors a time delay between a capacitor discharge instant and a spark start instant, according to a voltage waveform monitored at an input to said electrodes and further adjusts the input voltage according to the time delay using a drop time delay calibration graph.

5. The apparatus of claim 1 wherein said controller module further monitors a voltage tilt that occurs between a capacitor discharge instant and a spark start instant.

6. The apparatus of claim 5, wherein said controller module further adjusts the input voltage according to the voltage tilt using a predefined voltage tilt calibration graph.

7. A controller mediated method for providing constant pressure extracorporeal shock-waves in a shock wave generating device having a controller and spark gap electrodes, the method comprising:

measuring at least one factor related to burnout or erosion of said spark gap electrodes over time; and adjusting an output voltage of a voltage pulse generator in electrical communication with said spark gap electrodes according to said at least one factor in relation to any one of, or any combination of-one or more predetermined calibration graphs selected from the group consisting of: shock number calibration graph, an inter electrode gap calibration graph, a drop time delay calibration graph, and a voltage tilt calibration graph, and wherein said adjustment is facilitated by said controller.

8. An electrohydraulic shock-wave therapy apparatus providing constant pressure extracorporeal shock-waves, the apparatus comprising a high voltage power supply that is functionally coupled to and charges a high voltage capacitor;

wherein said capacitor is functionally connected to a spark plug wherein said connection is mediated with a pulse generator;

said spark plug having two common axis electrodes separated by a narrow gap between tips of the electrodes, said tips of said electrodes provided to generate said constant pressure extracorporeal shock-waves to form generated constant pressure extracorporeal shock-waves when said capacitor is discharged;

said pulse generator having a high voltage gated spark gap switch utilized to cause said capacitor to discharge into said spark plug; wherein said pulse generator is controlled with a controller module for adjusting an input voltage provided to said spark plug; wherein said controller module monitors a number of said generated constant pressure extracorporeal shock-waves;

wherein said spark plug is positioned adjacent to a concave reflector surface such that said generated constant pressure extracorporeal shock-waves expand radially from said spark plug and strike said concave reflector surface utilized to focus and transfer said generated constant pressure extracorporeal shock-waves toward a focal point;

a pressure transducer for measuring shock-wave pressure to form a measured pressure and transferring a measured pressure value to said controller module;

wherein the apparatus is characterized in that said controller module automatically controls and adjusts the input voltage provided to said spark plug, in order to compensate for electrode erosion of said tips without movement of said tips; and wherein said input voltage is controlled according to the measured pressure value and the number of generated constant pressure extracorporeal shock waves using a predefined shock number calibration graph, wherein automatic control and adjustment of the input voltage occurs substantially in real time.

9. The apparatus of claim 8 further comprising a gauge for measuring an inter electrode gap width and transferring a measured width value to said controller module, wherein said controller module further adjusts the input voltage according to the measured inter electrode gap width value using a predefined inter electrode gap calibration graph.

10. The apparatus of claim 9, wherein said gauge comprises an optical measuring device.

11. The apparatus of claim 8 wherein said controller module further monitors a time delay between a capacitor discharge instant and a spark start instant, according to a voltage waveform monitored at an input to said electrodes and further adjusts the input voltage according to the time delay using a drop time delay calibration graph.

12. The apparatus of claim 8 wherein said controller module further monitors a voltage tilt that occurs between a capacitor discharge instant and a spark start instant.

13. The apparatus of claim 12, wherein said controller module further adjusts the input voltage according to the-voltage tilt using a predefined voltage tilt calibration graph.

* * * * *